US00PP09974P

United States Patent [19]

van der Meer

[11] Patent Number: Plant 9,974

[45] Date of Patent: Jul. 22, 1997

[54] HYBRID TEA ROSE PLANT NAMED 'SELAURUM'

[75] Inventor: Peter Johannes Antonius van der Meer, Uithoorn, Netherlands

[73] Assignee: Terra Nigra Holding BV, De Kwakel, Netherlands

[21] Appl. No.: 610,396

[22] Filed: Mar. 4, 1996

[51] Int. Cl.[6] ..... A01H 5/00

[52] U.S. Cl. ..... Plt./21

[58] Field of Search ..... Plt./20, 21

*Primary Examiner*—Howard J. Locker

[57] ABSTRACT

A new rose variety of the Hybrid Tea class, characterized by its continuous good production of large dark red flowers having a very good presentation, borne singly on upright stems on a bush of medium height (120-150 cm), with a stem covering amount of foliage.

2 Drawing Sheets

BACKGROUND OF THE INVENTION

The present invention relates to a new and distinct variety of rose plant of the Hybrid Tea class, which was originated by me by crossing the variety 'Vivaldi' with an unnamed seedling (SR 85.018). The female parent 'Vivaldi' is light pink. 'Vivaldi' is shorter than 'Selaurum' and its leaves are lighter green. The male parent (SR 85.018) is also red but not as dark red as 'Selaurum' is. 'Selaurum' has a better vaselife and a better quality of the leaves. The primary objective of this breeding was to obtain a new large type rose with a good presentation and budshape in a trendy color. Among the novel characteristics possessed by the new variety which distinguish it from its parents and all other varieties of which I am aware are:

1) A large flower and flowerbud;

2) The very dark red color of the flower;

3) Rapid flowering cycles;

4) Good vaselife of the cutflower; and

5) A vigorous upright plant of medium height.

Asexual reproduction of the new rose variety by cutting and grafting using *R. canina* 'Natal Briar' as rootstock, as performed in a greenhouse in De Kwakel, The Netherlands, shows that the aforementioned characteristics and distinctions come true to form and are established and transmitted through succeeding propagations.

BRIEF DESCRIPTION OF THE DRAWINGS

The new variety of rose plant is illustrated by the accompanying photographic illustrations, of which Sheet 1 shows a full face view of the flower and Sheet 2 shows typical specimens of the vegetative growth and flowers of the new variety in different stages of development and as depicted in color as nearly true as it reasonably possible to make the same illustration of this character. The following is a detailed description of this new variety with color terminology in accordance with The Royal Horticultural Society Colour Chart (R.H.S.C.C.). The terminology used in the color description herein refers to plate numbers in the aforementioned color chart e.g. "55C" is plate "55C" of The Royal Horticultural Society Colour Chart.

Parentage: Seedling.

*Seed parent.*—'Vivaldi'.

*Pollen parent.*—unnamed seedling (SR 85.018).

Classification:

*Commercial.*—Hybrid Tea. cl BOTANICAL DESCRIPTION OF THE PLANT

Flower (Observations made from specimens grown in a greenhouse in De Kwakel, The Netherlands)

Blooming habit of 'Selaurum': Almost continuous.

A. Bud:

(1) *Size.*—Large. Diameter 2.0 – 2.5 cm. Length 4.5 – 5.0 cm.

(2) *Form.*—Pointed; is not affected by wet or hot weather.

(3 ) *Color.*—When the sepals first divide, the color of the outside is 46A.

(4) *Sepals.*—Length: 34 to 38 mm. Hooded over, curl back when petals start to unfurl. Color: inside: 139C. outside: 138B.

(5) *Calyx.*—Color: 138B. Shape: pear. Size: broad. Aspect: tiny hairs. Odor when rubbed: present.

(6) *Rate of opening.*—Normal.

(7 ) *Peduncle.*—Length: medium, 8 to 9 cm. Aspect: tiny hairs. Strength: medium. Color: 141C.

(8) *Opening.*—Opens up well; is not affected by adverse weather.

B. Bloom:

(1 ) *Size.*—Large; when fully expanded about 12 cm in diameter with a depth of about 7cm.

(2) *Borne.*—Single.

(3) *Stems.*—Length: long. Strength: strong.

(4) *Form (when first open).*—Round. Permanence: will flatten when aging.

(5) *Petalage.*—Number of petals: average 32.

(6) *Color.*—center of flower: 45A. Outer petals: 46A. Base of petals: 46l A. Spot at the base: very small, 3B. Inside of petals: 46A. Reverse of petals: 46A. General tonality: 46A.

(7) *Discoloration.*—General tonality 46A aging to a darker shade of 46B.

C. Petals:

(1) *Texture.*—Leathery; not affected by wet or hot weather.

(2) *Appearance.*—Inside: satiny. Outside: Shiny.

(3) *Form.*—Circular. Strong reflexing of margin. Strong undulation of margin.

(4) *Arrangement.*—Regular.

(5) *Petaloids in center.*—Absent.

(6) *Persistence.*—Drop off cleanly.

(7) *Fragrance.*—Absent.
(8) *Lasting quality.*—On the plant: good. As cutflower: average 12 days.

Reproductive Organs

A. Stamens:
(1) *Arrangement.*—Regularly arranged around styles.
(2) *Number.*—Average close to 120.
(3) *Length.*—10 to 14 mm.
(4) *Anthers.*—Size: small, 2 to 4 mm. Color: pale brown, approx. 161A.
(5) *Filaments.*—Length: medium, 10 to 12 mm. Color: 52B, base of filament yellow 4A.
(6) *Pollen.*—Color: pale brown.

B. Pistils:
(1) *Styles.*—Number: average close to 120. Length: 7 to 12 mm. Color: white flushed with 63B and 63C.
(2) *Stigmas.*—Color: light yellow, 11C.
(3) *Fruit.*—Fertility: unknown. Fruits/hips: not observed.

Plant

A. Form: Greenhouse rose.
B. Growth: Vigorous upright.
C. Height: Medium, 120 to 150 cm.
D. Foliage: Compound of 3, 5 or 7 leaflets. Average 8 to 10 compound leaves on bloom stem, 10 to 12 on main canes.
(1) *Size.*—Medium.
(2) *Quantity.*—Average, stem covering.
(3) *Color.*—New foliage: upper side: 139A. under side 148C. Old foliage: upper side: 143 A. under side: 138 C.
(3 ) *Texture.*—Upper side: dull, smooth. Under side: dull, smooth.
(4) *Terminal leaflet.*—Shape: oval pointed, base rounded to cordate. Size: large. Length 100 to 110 mm. Maximum diameter 65 to 70 mm. Length petiole 15 to 25 mm.
(5) *Ribs and veins.*—Anthocyanin coloration in veins.
(6) *Rachis.*—Upper side: smooth with very few and very small glandular hairs, anthocyanin colored. Lower side: average 3 prickles per compound leaf, about 4 mm of size and hooked downward.
(7) *Margin type.*—Very serrate, 4 points/cm, 2 mm peak.
(8) *Stipules.*—Length: average 15 mm, auricle to 5 mm. Texture: smooth. Color: 143A.

E. Resistance to diseases: Average disease resistance.
F. Wood:
(1) *New wood.*—Color: purple brownish, 183A. Bark: smooth.
(2) *Old wood.*—Color: green purple, 146B striped with 59A. Bark: smooth.

G. Thorns:
(1) *Quantity.*—Medium. On main stalks from base: medium.
(2) *Form.*—Upperside flat, lower side concave.
(3) *Length.*—Large, 12 mm.
(4) *Hooked.*—Little downward.
(5) *Color (when young).*—Bronze/purple, 178A.
(6) *Position.*—Irregular.

H. Prickles:
*Quantity.*—Medium, on peduncle: just above 1st compound leaf. On rachis: about 3 per compound leaf.

I. Short needles:
*Quantity.*—None or very few.

I claim:

1. A new and distinct variety of rose plant of the Hybrid Tea class named 'Selaurum', substantially as herein shown and described, characterized particularly as to novelty by its characteristics enumerated above.

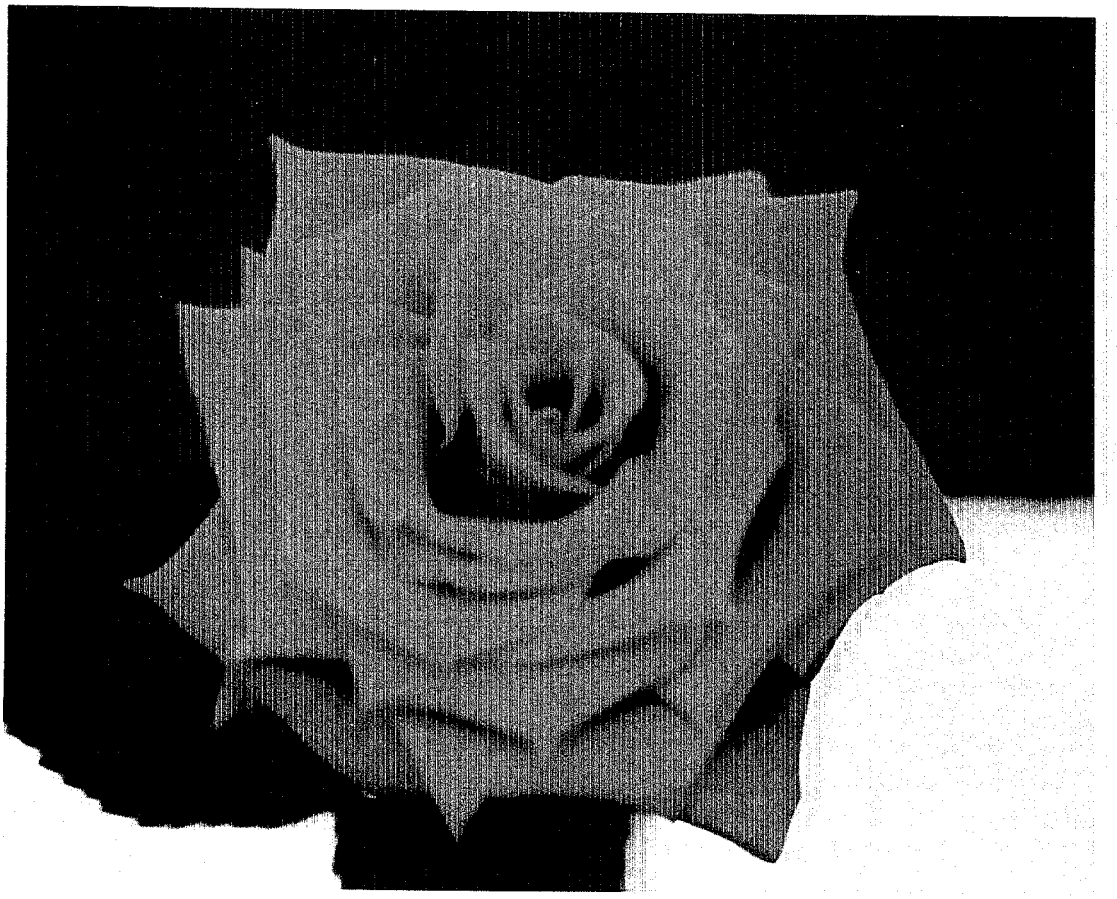

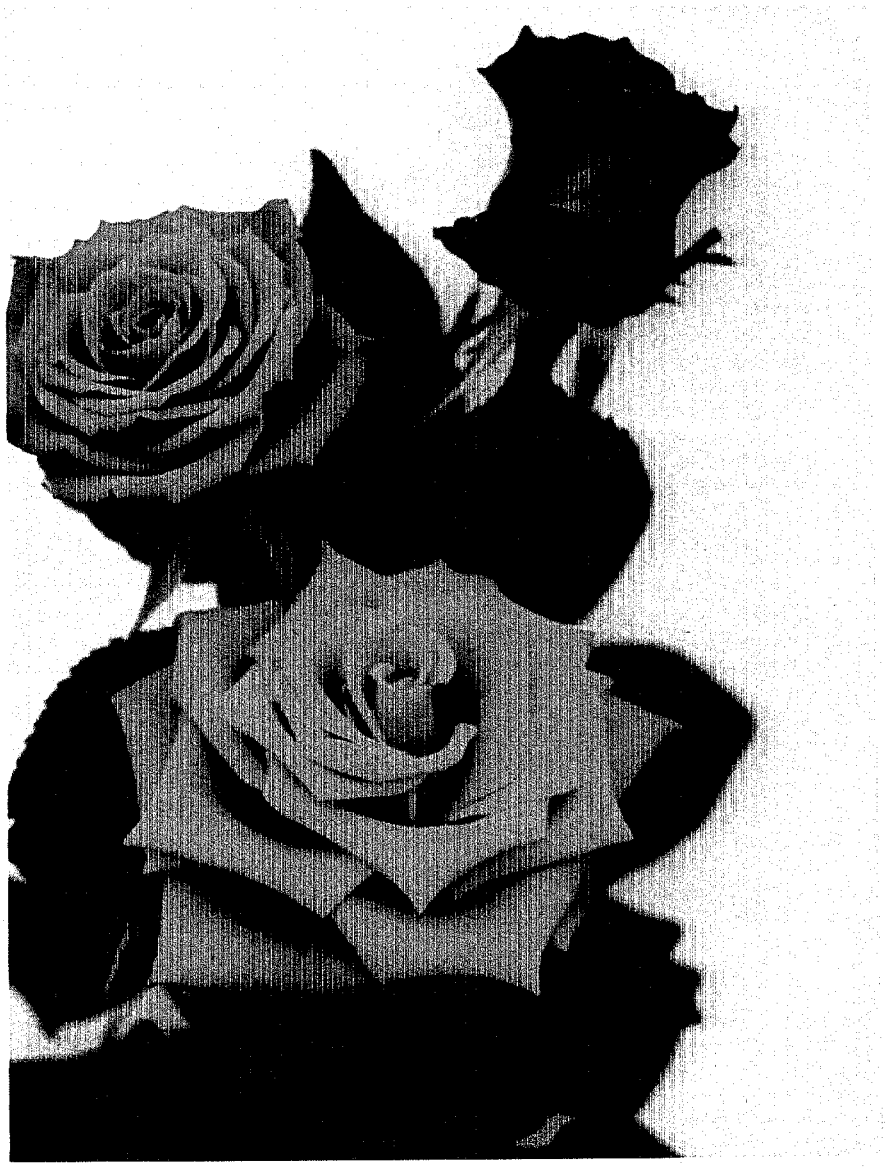

* * * * *